US008323207B2

(12) United States Patent
Popov et al.

(10) Patent No.: US 8,323,207 B2
(45) Date of Patent: Dec. 4, 2012

(54) METHOD AND DEVICE FOR MEASUREMENT OF EXHALED RESPIRATORY GAS TEMPERATURE

(75) Inventors: Todor Alexandrov Popov, Sofia (BG); Stefan Stefanov Dunev, Sofia (BG)

(73) Assignee: Delmedica Investments Limited, Road Town, Tortola (VG)

( * ) Notice: Subject to any disclaimer, the term of this patent is extended or adjusted under 35 U.S.C. 154(b) by 1348 days.

(21) Appl. No.: 11/996,963

(22) PCT Filed: Jun. 12, 2006

(86) PCT No.: PCT/IB2006/001677
§ 371 (c)(1),
(2), (4) Date: Jan. 26, 2008

(87) PCT Pub. No.: WO2007/012930
PCT Pub. Date: Feb. 1, 2007

(65) Prior Publication Data
US 2008/0228098 A1 Sep. 18, 2008

(30) Foreign Application Priority Data
Jul. 27, 2005 (BG) ........................ 109243

(51) Int. Cl.
*A61B 5/08* (2006.01)
(52) U.S. Cl. ........................ 600/537; 600/529
(58) Field of Classification Search ........................ None
See application file for complete search history.

(56) References Cited

U.S. PATENT DOCUMENTS

| 4,453,552 A | | 6/1984 | Ensign et al. | |
|---|---|---|---|---|
| 5,179,958 A | * | 1/1993 | Mault | 600/531 |
| 5,518,002 A | * | 5/1996 | Wolf et al. | 600/538 |
| 2004/0107986 A1 | * | 6/2004 | Neilson et al. | 136/204 |

FOREIGN PATENT DOCUMENTS

| JP | 11033119 | 2/1999 |
|---|---|---|
| SU | 1 110 440 A | 8/1984 |
| WO | WO 00/36976 A | 6/2000 |

OTHER PUBLICATIONS

Clary, et al., "Fast-Responding Automated Airway Temperature Probe," Medical and Biological Engineering and Computing, Springer, Heidelberg, Germany, vol. 29, No. 5, Sep. 1, 1991, pp. 501-504.
International Search Report and Written Opinion for PCT Patent Application No. PCT/IB2006/001677, dated Sep. 8, 2006.

* cited by examiner

*Primary Examiner* — Agnieszka Boesen
(74) *Attorney, Agent, or Firm* — Gomez Int'l Patent Office, LLC

(57) ABSTRACT

An apparatus for the measurement of exhaled respiratory gas temperature during free voluntary tidal breathing, comprises a housing 1 defining a chamber, an air inlet 2 for receiving a stream of exhaled respiratory gas and an air outlet 4 for permitting escape of exhaled respiratory gas from the chamber to outside of the housing. A tube having inner and outer surfaces, is located within the housing and extends from the air inlet into the chamber provides a passageway through which the stream of exhaled respiratory gas may travel from the air inlet in to the chamber. A temperature sensor 6 is located within the housing for measuring the temperature of exhaled respiratory gas. The air inlet, temperature sensor and air outlet are configured such that in use the stream of exhaled respiratory gas traveling within the housing contacts with at least part of the inner surface of the tube when the respiratory gas is traveling upstream of the temperature sensor and contacts with at least part the outer surface of the tube when the stream of respiratory gas is traveling downstream of the temperature sensor.

17 Claims, 2 Drawing Sheets

METHOD AND DEVICE FOR MEASUREMENT OF EXHALED RESPIRATORY GAS TEMPERATURE

Figure 1:
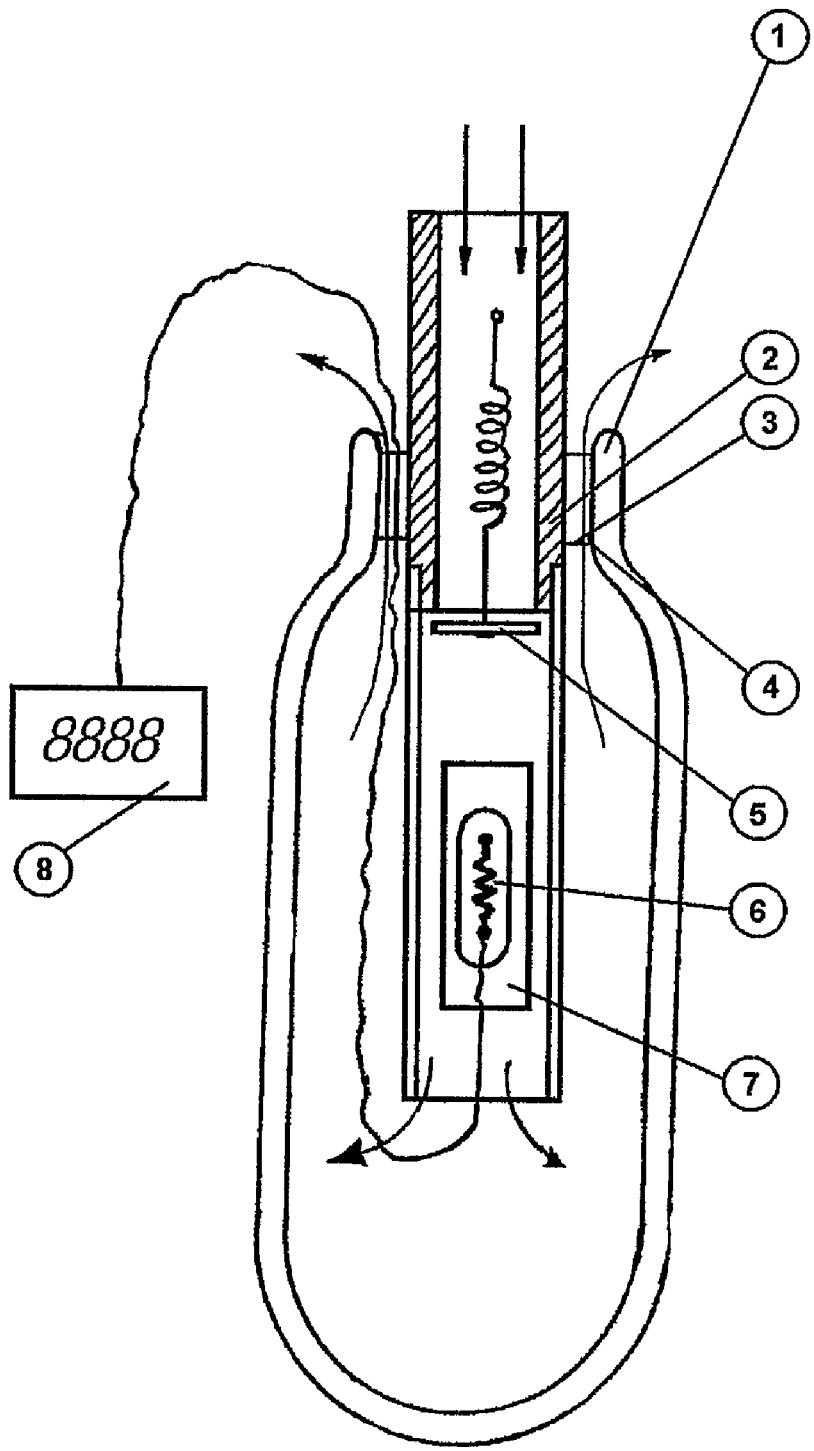

The present invention is concerned with a method and device for the measurement of the temperature of exhaled breath, such as may find application in medicine. More specifically, the present invention is concerned with an apparatus useful in the performance of different medical investigations, including diagnostics and prevention and treatment of inflammatory lung and airway illnesses, such as diseases and allergies, in which assessment of the temperature of the exhaled breath may prove useful for the purpose of diagnosis and monitoring of the effect of anti-inflammatory treatments.

It is known that one of the most frequent socially important non-communicable diseases, asthma, is due to allergic inflammation of the airways. Evidence to this end has been collected by means of invasive methods of investigation: bronchoscopy with broncho-alveolar lavage and biopsies. Studies have established a quantitative relationship between the degree of inflammation of the airways and asthma severity, and also between a dose of an anti-inflammatory treatment and an ensuing clinical effect. Bronchoscopy is associated with an unpleasant experience for patients and also bears some risk, both during and after the investigation. Consequently, bronchoscopy cannot be applied routinely for the evaluation of airway inflammatory processes so as to tailor a therapy for an individual patient. Non-invasive methods have been introduced as an alternative, for example, using examination of sputum, measurement of nitric oxide in exhaled air and assessment of mediators of inflammation in exhaled breath condensate. These approaches lack precision and consequently the results cannot reliably confirm a diagnosis or serve as a basis for treatment decisions. At the same time such non-invasive methods are time consuming and expensive. For example, measurement of nitric oxide in exhaled air, whose levels are higher in asthmatics, is complex, expensive and only suitable for use in specialized clinics.

Inflammation is a universal pathophysiological process and increased temperature is one of its five prominent features. In a patient with an inflamed airway, the inflamed airway mucosa acts to warm adjacent air to a higher level compared with the air adjacent to a comparative uninflamed mucosa. The extent of this warming of adjacent air depends upon the spread of an inflammatory region and on the level of inflammation.

U.S. Pat. No. 4,453,552, "Electronic indicator of body temperature" discloses a device and a method for measurement of the temperature of air exhaled by a patient. The device incorporates a tube, in which one end of a thermocouple is placed so as to be in contact with exhaled air from the patient. The other end of the thermocouple is positioned outside the tube and in contact with the ambient air. An electronic system analyzes the signal of the thermocouple and provides information about the temperature of the exhaled air. In U.S. Pat. No. 4,453,552 it is assumed that the temperature of the exhaled air is representative of body temperature, and is monitored on-line based upon this approach. Application of the device of U.S. Pat. No. 4,453,552 is in the field of reanimation and anesthesiology. However, the device of U.S. Pat. No. 4,453,552 when used as an indicator of body temperature has definite constructive deficiencies, as an open tube is used which allows ambient conditions, such as air drafts and the mode of breathing, to potentially influence the measurement of exhaled air temperature. Furthermore, the device of U.S. Pat. No. 4,453,552 measures an instantaneous temperature which can change throughout the breathing cycle, which may compromise the precision of the measurement.

Other devices for the measurement of the exhaled breath temperature are described in (1) Piacentini G L, Bodini A, Zerman L, et al. 'Relationship between exhaled air temperature and exhaled nitric oxide in childhood asthma', Eur Respir J 2002; 20: 108-111; and (2) Paredi P, Kharitonov S A, Barnes P J. 'Faster rise of exhaled breath temperature in asthma: a novel marker of airway inflammation?', Am J Respir Crit Care Med 2001; 165: 181-184.

The temperature of exhaled air has been measured using temperature sensors placed in front of the mouths of asthmatics in conjunction with nitric oxide measurements in those same patients. The temperature sensors used were fast reacting thermocouples, having a reaction time of 0.05 sec, placed in a plastic tube. These make possible temperature measurement at multiple time points during expiration. These devices represent open experimental systems allowing interference of exhaled breath temperature by ambient conditions and patient related factors, such as depth and rate of the breathing. In addition, the protocol for exhaled breath temperature is complicated. Hence, whilst these known sensors have enabled a relationship to be established between the quantity of the exhaled nitric oxide and the exhaled breath temperature there remains a need for a simple, precise and reliable apparatus and method for measuring the temperature of exhaled breath, such as for use in the diagnosis of respiratory ailments, for example asthma.

It is an object of the present invention to provide a method and device for measurement of the temperature of exhaled air, which allows a high level of precision of the measurement, and which is simple and convenient to use by a patient or investigator. The device should preferably be cost effective for routine application in medical practice, i.e. it should have a minimum of moving parts and comprise as few component parts as practicable.

The present invention, in its various aspects, is as set out in the accompanying claims.

In one aspect, the present invention provides an apparatus for the measurement of exhaled respiratory gas temperature during free voluntary tidal breathing, the apparatus comprising (i) a housing defining a chamber, an air inlet for receiving a stream of exhaled respiratory gas and an air outlet for permitting escape of exhaled respiratory gas from the chamber to outside of the housing, (ii) a tube having inner and outer surfaces, the tube being located within the housing and extending from the air inlet into the chamber, thereby providing a passageway through which the stream of exhaled respiratory gas may travel from the air inlet in to the chamber, and (iii) a temperature sensor located within the housing for measuring the temperature of exhaled respiratory gas, such as when the stream of respiratory gas passes the temperature sensor, characterised in that the air inlet, temperature sensor and air outlet are configured such that in use the stream of exhaled respiratory gas traveling within the housing contacts with at least part of the inner surface of the tube when the respiratory gas is traveling upstream of the temperature sensor and contacts with at least part the outer surface of the tube when the stream of respiratory gas is traveling downstream of the temperature sensor.

In another aspect, the present invention provides a method for determining the temperature of exhaled respiratory gas during free voluntary tidal breathing, the method comprising the steps:

i) providing a patient with an apparatus as described above;

ii) the patient exhaling into the air inlet of a said apparatus until the apparatus reaches thermal equilibrium as determined by a stable temperature reading derived from the temperature sensor of the apparatus;

iii) recording said temperature reading.

The present invention provides a number of advantages. The apparatus enables exhaled respiratory gas to contact at least part of both the inner and outer surfaces of the tube which, in turn, assists the apparatus to reach temperature equilibrium during use and a more reliable measurement of breath temperature to be achieved.

In the apparatus of the invention, the tube may be provided with an extension tube, comprising an inner and outer surface, which extends away from the air inlet outside of the housing. This extension tube may itself be used as a mouthpiece for ease of blowing into the apparatus or, if required, as a convenient attachment point for a disposable mouthpiece. Preferably, the apparatus is so configured that exhaled respiratory gas escaping from the chamber through the air outlet is directed towards the outer surface of the extension tube. This preferred configuration helps prevent or reduce the effect of draughts and other sources of cold air impinging directly upon the tube extension, and so assists the apparatus to reach temperature equilibrium during use and a more reliable measurement of breath temperature to be achieved.

In the apparatus of the invention, the air outlet preferably surrounds at least a portion of the inlet airway. More preferably, the air outlet substantially surrounds the inlet airway i.e. the air outlet may be concentric about at least a substantial part of the air inlet. This preferred arrangement assists the apparatus to reach temperature equilibrium during use and a more reliable measurement of breath temperature to be achieved.

The apparatus of the invention may comprise a one-way valve for preventing flow of respiratory gas out of the inlet airway and/or the apparatus may comprise a one-way valve for preventing atmospheric air from flowing into the chamber through the outlet airway. This helps prevent air inadvertently being sucked in a reverse direction through the apparatus, which would otherwise prevent the apparatus from reaching temperature equilibrium during use.

The temperature sensor used in the apparatus of the invention is preferably located in the passageway inside the tube or in the chamber such that in use it is contacted by the stream of exhaled respiratory gas. Preferably, the temperature sensor is located in the passageway inside the tube, thereby placing it close to the source of the stream of exhaled respiratory gas and remote from the air outlet.

Preferably, the temperature sensor is either attached directly to the inner or outer surface of the tube, preferably the inner surface, or it is suspended in the passageway inside the tube.

In the apparatus of the invention, all or part of the tube extending within the chamber is formed from a material which preferably has a high thermal conductivity. The thermal energy transferred to the tube by the incoming and outgoing stream of respiratory gas is therefore distributed evenly throughout the tube. Preferably, the temperature sensor is located in thermal communication with the tube so that the sensor itself similarly avoids recording an unrepresentative high or low temperature.

Preferably, the temperature sensor is provided with a thermal reservoir.

The provision of a thermal reservoir for the temperature sensor is preferred because, during the time the apparatus takes to reach thermal equilibrium, short term fluctuations in respiratory gas temperature may be evened out and a patient becomes accustomed to using the apparatus correctly, a temperature reading more representative of breath temperature is therefore obtainable. In one embodiment, the thermal reservoir may be provided by all or part of the tube within the chamber. In another embodiment, the thermal reservoir may be provided by a a block or strip of an appropriate material, e.g. a metal such as aluminium. In another embodiment, the thermal reservoir may be provided by a block or strip and at least a part of the tube within the chamber. Given the apparatus and the requirement for the apparatus to reach thermal equilibrium in a reasonable time, a person skilled in the art will readily be able to provide an appropriate thermal reservoir for the temperature sensor. Typically, however, the thermal reservoir will have a heat capacity equivalent to the heat capacity of an aluminium cube having a weight of from 3 to 81 g, preferably from 30 to 50 g.

In the present invention the term thermal conductivity refers to thermal conductivity such as may be quantified in units of $Wm^{-1}K^{-1}$. A material with a high thermal conductivity is a material having a thermal conductivity greater than that of polyethylene, such as metals, e.g. aluminum and copper. A preferred example is aluminum. Preferably, the thermal conductivity of the material forming the tube is at least 1, more preferably at least 10, even more preferably at least 40, most preferably at least 200, $Wm^{-1}K^{-1}$ at 23° C.

The apparatus of the present invention may comprise a thermistor or thermocouple as a temperature sensor. A thermistor is preferred. The temperature sensor may be electrically connected to an electronic processing unit and display for providing an indication to a user of the temperature of the respiratory gas inside the apparatus. The electronic processing unit preferably comprises means to indicate when thermal equilibrium has been reached, at which time an accurate temperature reading may be obtained.

In the present invention, the housing serves to thermally insulate the chamber from external atmospheric conditions. In one embodiment, the housing may comprise a Dewar flask. In another embodiment, the housing is formed from a plastics material having low thermal conductivity. Preferably, the thermal conductivity of the housing is no greater than 0.5, more preferably no greater than 0.1, even more preferably no greater than 0.05, most preferably no greater than 0.025, $Wm^{-1}K^{-1}$ at 23° C. A thermally insulative housing assists the apparatus to reach temperature equilibrium during use and a more reliable measurement of breath temperature to be achieved.

In the present invention the term free voluntary tidal breathing refers to breathing which is not externally aided, such as by a respirator.

The time required for the apparatus to reach equilibrium during use is preferably no more than 10 minutes, more preferably no more than 5 minutes, and may be less than 2 minutes.

In yet another aspect, the present invention provides a method of controlling an inflammatory respiratory illness, such as a disease or allergy, e.g. asthma, in a patient known to suffer from said inflammatory respiratory illness, the method comprising:

a) measuring the exhaled breath temperature of the patient;

b) calculating the difference between the exhaled breath temperature of the patient as measured in step a) and a predetermined known normal exhaled breath temperature of the patient, which predetermined known normal exhaled breath temperature of the patient was determined from a plurality of exhaled breath temperature measurements obtained from the patient at times when the patient was not known to be suffering from acute symptoms of the inflammatory respiratory illness; and, either c)i) when the calculated difference between the exhaled breath temperature of the patient as measured in step a) and the predetermined known normal exhaled breath temperature of the patient is equal to or less than a first predetermined amount, either contacting the patient with no medicament or with a first medicament for treating the inflammatory respiratory illness; or c)ii) when the calculated difference between the exhaled breath temperature of the patient as measured in step a) and the predetermined known normal exhaled breath temperature of the patient is greater than a first predetermined amount, contacting the patient with a second medicament for treating the inflammatory respiratory illness. When the calculated difference between the exhaled breath temperature of the patient as measured in step a) and the predetermined known normal exhaled breath temperature of the patient is greater than a second predetermined amount, e.g. by more than 1° C., the method may comprise contacting the patient with a third medicament for treating the inflammatory respiratory illness. Accurate measurement of the exhaled breath temperature may be achieved through the use of the apparatus of the present invention.

For example, if the difference between the temperature of the exhaled breath of a patient known to suffer from asthma is found to be no greater than 0.5° C. above the predetermined known normal exhaled breath temperature of the patient, the diagnosis of the patient's condition may be such that no change is required to the patient's treatment i.e. no medicament treatment is required at all or, if the patient is already being treated with a first medicament, no change of treatment is required. If, however, the difference between the temperature of the exhaled breath of a patient known to suffer from asthma is found to be greater than 0.5° C. above the predetermined known normal exhaled breath temperature of the patient, the diagnosis of the patient's condition may be such that the patient is potentially liable to an asthma attack and that, as a precautionary measure to avoid such an attack, a change is effected to the patient's treatment i.e. the patient is treated with a second medicament. Treatment with the second medicament can be continued until such time as the patient's exhaled breath temperature is measured to be below the 0.5° C. maximum above the predetermined known normal exhaled breath temperature, when the patient may return to either requiring no medicament or treatment with the first medicament.

The ability for a medical practitioner, skilled patient or other skilled user to determine small changes in exhaled breath temperature is seen to be potentially beneficial as a means of offering early control of inflammatory respiratory illness, which illnesses may be observed first by small but significant changes in exhaled breath temperatures which occur before the patient is observed to suffer acute symptoms of the illness. Further, the present invention enables a patient to be treated with different medicaments (e.g. different active pharmaceuticals or different concentrations of the same active pharmaceuticals) depending upon the criticality of the treatment required as determined by the size of the difference between the measured exhaled breath temperature and the predetermined normal.

Figure 2:
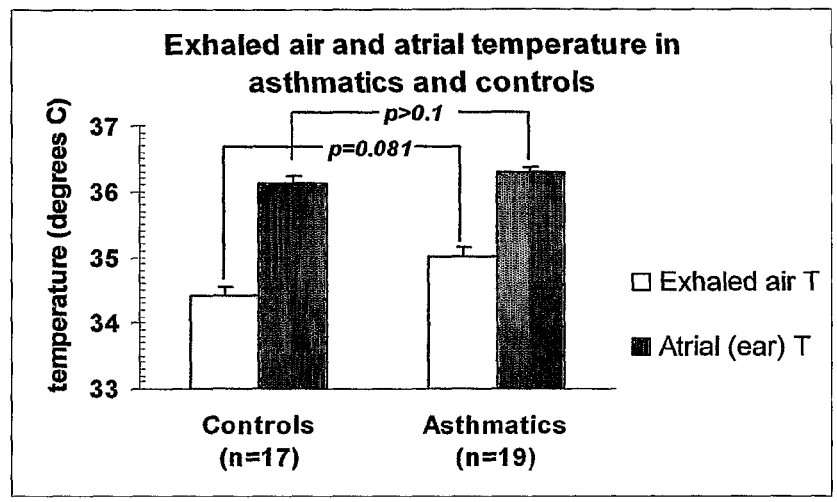
Figure 3:
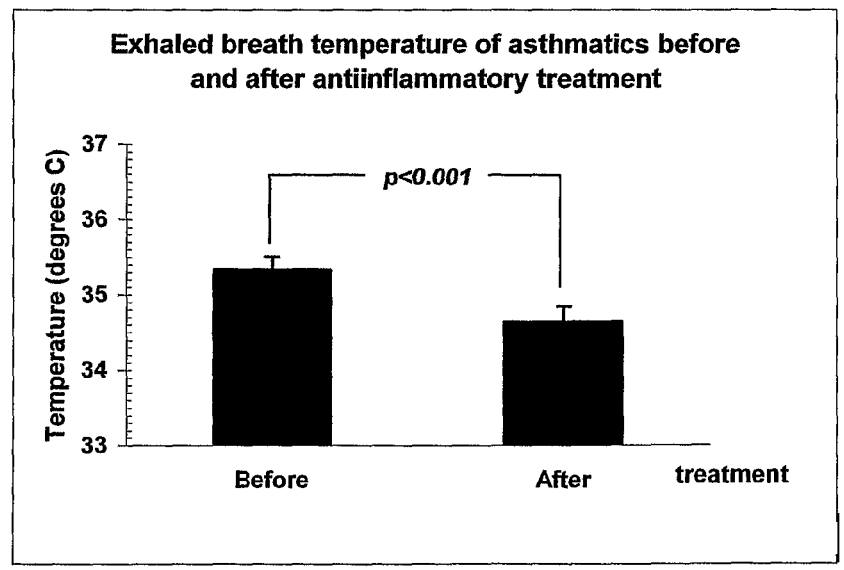

The invention, in its various embodiments, shall now be further described by way of example and with reference to the drawings, in which FIG. 1 is a cross-section of an apparatus in accordance with the present invention;

FIG. 2 is an illustration showing how exhaled breath temperature may differ from ear temperatures; and FIG. 3 is an illustration showing how exhaled breath temperatures may differ in a patient suffering from asthma before and after treatment.

A protocol for exhaled air temperature measurement during free voluntary tidal breathing is as follows. The subject inhales through the nose room air which is preferably within the temperature range 18°-22° C. and then exhales into the air inlet of the device. Measuring the resistance of a thermal sensor assesses the temperature in the thermal chamber. It is increased by the cumulative effect of multiple exhalations on the part of the examined subject. The measurement continues until temperature equilibrium is established within this closed system between the temperature of the exhaled air and the temperature of the metal core (or block) inside the thermal chamber.

The method may be performed using an apparatus of the invention which incorporates a thermo-isolated bottle-like vessel, or housing, with a mouthpiece at its opening, with a heat accumulating metal core with a thermal sensor attached thereto and a valve preventing the subject from inhaling from the chamber.

In one embodiment of the apparatus, the vessel represents the housing of a thermally insulated chamber constructed as a Dewar flask, also termed a vacuum flask, with a mouthpiece positioned into an in-going tube situated in an, in use, upper part of the chamber. The tube is fixed to the mouth of the Dewar vessel by means of an element with outlets. In the interior of the tube from top to bottom are situated a reverse valve and temperature sensor, mounted on a metal core; the sensor is linked to a reading device outside the chamber.

The number of outlets could be changed so as to allow appropriate resistance to optimally modulate the rate of breathing.

The device of the present invention features simplified and robust construction. It allows subjects to measure the temperature of their exhaled air in an easy and convenient way. The thermally isolated Dewar vessel enables the incoming exhaled air to impart its thermal energy to the high thermal capacity metal core and the attached thermal sensor within the time frame until the next exhalation. Adding up of subsequent exhalations allows achievement of a thermal balance mostly independent of the ambient conditions and reflective of the integral temperature within the lungs. A chance interruption of the breathing rhythm (swallowing or pausing on the part of the subjects) does not bear any significant effect on the final result. The device could be applied as individual gauge for subjects with airway inflammatory disease to monitor the course of their disease and to help timely modifications of the treatment scheme and prevent exacerbations.

The device of the present invention may comprise a processor to automatically monitor the progress of the measurement, to produce an indication, such as sound, when thermal equilibrium is reached and to present the measured temperature on a display on an external surface or body of the device.

The device of the present invention could be used in practice to give the user initial information about the exhaled breath temperature of a given patient with inflammatory airway disease, to be further used as reference in the course of treatment. The device of the present invention may be operated by a patient or by medical personnel. The device of the present invention may also comprise means for storing measurements and may allow measurements taken on a regular basis, such as day-to-day, basis to be stored in a database to help the doctor or the patient take a needed action.

An example of the method of the present invention to measure exhaled breath temperature involves at least 5 subsequent assessments. The patient breathes out through a mouthpiece into a thermal chamber, whose temperature is determined by the readings of the electrical resistance of a temperature sensor, and can be seen on a display. The values keep changing until the temperature in the thermal chamber reaches equilibrium with the temperature of the air exhaled by the subject. When such a plateau is reached, the corresponding temperature is marked as the temperature of the exhaled breath of the tested subject.

The method of the invention is made possible by means of a device built to this purpose. FIG. 1 represents a schematic drawing of an exemplary embodiment of the device for exhaled air measurement. The device comprises a thermal chamber or housing made as a Dewar vessel (1), with an inlet tube (2) in its upper part fixed by means of a tightening or securing element (3) with in built air outlets orifices (4). It is preferable that the thermal chamber has an elongated cylindrical shape softly folding to form its bottom part with the shape of a hemisphere. This shape will ensure smooth flow of the exhaled air and avoid turbulences. The number of outlet holes may vary to achieve optimal aerodynamic resistance favoring the desired breathing rate. In the interior of the air inlet tube (2) from top to bottom are situated one way or reverse valve (5) and temperature sensor (6), mounted on a metal core (7); the sensor is linked to a reading device (8) situated outside the chamber (1). The temperature sensor is calibrated in two points within the range 0°-36° C. The temperature of the thermal chamber is assessed by determining the electrical resistance (Ohms) of the temperature sensor, which is in the form of a thermistor. When working with the created prototype, the investigator recorded the resistance values at one-minute intervals and discontinued the measurement when the last registered value was the same as the preceding one. The time for achieving thermal equilibrium was within the range of 5 to 12 minutes.

The essence of the invention is that a thermal reservoir is heated by exhaled air. Each subsequent exhalation increases the inside temperature until an equilibrium is reached. As the reservoir has a relatively high volume, minimal and short temperature changes (artifacts) do not affect significantly the end result. It is recommended that the measurement is made at room temperature (18°-22° C.), which ensures reproducible and reliable results. The device is made ready for measurement by placing a mouthpiece in the inlet tube. The subject holds it with one or both hands, breathes in through the nose and breathes out through the mouthpiece at a rate he or she finds comfortable. He or she is advised against hyperventilation and is allowed to make short pauses to swallow or make verbal comment. The investigator marks the readings of the ohmmeter in a report form at minute intervals until a value repeats itself. Then the value is converted to the corresponding temperature following a formula worked out when initial calibration of the device was made. When the measurement is complete, the device is dissembled, cleaned with cool water, dried and assembled for the next measurement.

A device of the invention as described above was used to measure exhaled breath temperature. The device was tested in its day-to-day reproducibility using 11 healthy controls. The measurements were at room temperature of between 19° C. and 22° C. The statistical results are tabulated in table 1.

We measured the exhaled breath temperature of 11 subjects (4 men and 7 women, age range 20÷65 years) without signs of respiratory disease and compared it to their axillary and aural (ear) temperature.

The day-to-day reproducibility in healthy subjects calculated as intraclass correlation coefficient was 0.991. The reproducibility of ear and auxiliary temperatures measured in parallel was much lower, suggesting that exhaled breath temperature is a different and more consistent physiological variable. The correlation of exhaled breath temperature with ear and axilla temperature was low, suggesting that it is measuring a different and more consistent physiological variable

TABLE 1

Reliability Statistics

| | |
|---|---|
| Common Mean | 34.104 |
| Common Variance | 1.418 |
| True Variance | 1.407 |
| Error Variance | 0.011 |
| Common Inter-Item Correlation | 0.991 |
| Reliability of Scale | 0.996 |
| Reliability of Scale (Unbiased) | 0.997 |

In a further study device was also assessed in its ability to discriminate between healthy controls (n=17) and asthmatics (n=19), and also its capacity to detect changes in asthma control in 14 asthmatics before and after antiinflammatory treatment.

We compared the exhaled breath temperature of 17 subjects (5 men and 12 women, age range 20÷65 years) without signs of respiratory disease and of 19 outpatients with asthma (8 men and 11 women, age range 17÷45 years) with different levels of disease severity and control.

We measured the exhaled breath temperature of 14 asthmatics (6 men and 8 women, age range 17÷65 years) hospitalized for exacerbations of their asthma and treated with systemic steroid for 7 days.

A further trial of the apparatus of the invention was performed as follows.

There was a difference between the exhaled air temperature of asthmatics (mean 34.41±s.e.m. 0.27° C.) and controls (35.02±0.21° C.), but there was considerable overlap (p=0.081). There was a significant difference between the exhaled air temperature of asthmatics before (35,33±0.17° C.) and after improvement under treatment (34,64±0.21° C.), (p<0.001). It should be stated that most of the asthmatics studied were relatively well controlled on inhaled corticosteroids.

There was a significant difference between the exhaled breath temperature of asthmatics before (mean 35,33±s.e.m. 0.17° c) and after improvement under anti-inflammatory treatment (34,64±0.21° c), (p=0.000). The results of this trial are shown in FIGS. 2 and 3.

A device of present invention is preferably provided with a disposable mouth piece for insertion into or placing over a mouth of a patient. A disposable mouth piece is preferable on hygiene grounds. The present invention by warming an incoming airway may also warm a mouth piece portion of an incoming airway. As this warming is by redirected backflowed air from the device of the invention, the present invention realizes a convenient method of warming a mouthpiece entrance without providing any additional ducting or separate heating element. As described above, the heating of an incoming airway with backflowed air provides a more reliable measurement of breath temperature, especially when combined with a device portion of high heat capacity in proximity to the temperature sensor.

The invention claimed is:

1. An apparatus for the measurement of exhaled respiratory gas temperature during free voluntary tidal breathing, the apparatus comprising (i) a housing defining a chamber, an air inlet for receiving a stream of exhaled respiratory gas and an air outlet for permitting escape of exhaled respiratory gas from the chamber to outside of the housing, (ii) a tube having inner and outer surfaces, the tube being located within the housing and extending from the air inlet into the chamber, thereby providing a passageway through which the stream of exhaled respiratory gas may travel from the air inlet in to the chamber, and (iii) a temperature sensor located within the housing for measuring the temperature of exhaled respiratory gas, characterised in that the air inlet, temperature sensor and air outlet are configured such that in use the stream of exhaled respiratory gas traveling within the housing contacts with at least part of the inner surface of the tube when the respiratory gas is traveling upstream of the temperature sensor and contacts with at least part the outer surface of the tube when the stream of respiratory gas is traveling downstream of the temperature sensor.

2. The apparatus as claimed in claim 1, wherein the apparatus further comprises an extension tube, comprising an interior and exterior surface, which connects with and extends away from the air inlet outside of the housing.

3. The apparatus as claimed in claim 2, wherein the air outlet is so configured that exhaled respiratory gas escaping from the chamber through the air outlet is directed towards the exterior surface of the extension tube.

4. The apparatus as claimed in claim 1, wherein the temperature sensor is located inside the tube.

5. The apparatus as claimed in claim 1, wherein all or part of the tube has high thermal conductivity.

6. The apparatus as claimed in claim 1, wherein all or part of the tube extending within the chamber has high heat capacity.

7. The apparatus as claimed in claim 1, wherein the apparatus further comprises a one-way valve for preventing airflow out through the air inlet and/or a one-way valve for preventing airflow in through the air outlet.

8. The apparatus as claimed in claim 7, wherein a one way valve for preventing airflow out through the air inlet is located in or on the tube upstream of the temperature sensor.

9. The apparatus as claimed in claim 1, wherein the temperature sensor comprises or is attached to a thermal reservoir of high heat capacity.

10. The apparatus as claimed in claim 9, wherein the thermal reservoir comprises a metal block.

11. The apparatus as claimed in claim 1, wherein the temperature sensor is a thermistor.

12. The apparatus of claim 1, further comprising an electronic processor for processing electronic signals from temperature sensor and a display for displaying signals from the processor.

13. The apparatus as claimed in claim 1, wherein the air outlet surrounds at least a portion of the air inlet.

14. The apparatus as claimed in claim 13, wherein the air outlet is concentric with at least part of the air inlet.

15. The apparatus as claimed in claim 1, wherein the air inlet and the air outlet are both present in a single aperture formed in the housing.

16. The apparatus as claimed in claim 1, wherein the housing serves to thermally insulate the chamber.

17. The apparatus as claimed in claim 16, wherein the housing comprises a Dewar flask.

* * * * *